United States Patent
Lange et al.

(10) Patent No.: US 12,378,176 B2
(45) Date of Patent: *Aug. 5, 2025

(54) PRE-TREATMENT OF LIGNOCELLULOSIC FEEDS FOR THE PRODUCTION OF GLYCOLS

(71) Applicant: SHELL OIL COMPANY, Houston, TX (US)

(72) Inventors: Jean Paul Andre Marie Joseph Ghislain Lange, Amsterdam (NL); Evert Van Der Heide, Amsterdam (NL); Pieter Huizenga, Amsterdam (NL); Thimo Daniel Jozef Te Molder, Enschede (NL)

(73) Assignee: Shell USA, INC., Houston, TX (US)

( * ) Notice: Subject to any disclaimer, the term of this patent is extended or adjusted under 35 U.S.C. 154(b) by 480 days.

This patent is subject to a terminal disclaimer.

(21) Appl. No.: 17/637,856

(22) PCT Filed: Sep. 25, 2020

(86) PCT No.: PCT/EP2020/077009
§ 371 (c)(1),
(2) Date: Feb. 24, 2022

(87) PCT Pub. No.: WO2021/058805
PCT Pub. Date: Apr. 1, 2021

(65) Prior Publication Data
US 2022/0281788 A1    Sep. 8, 2022

(30) Foreign Application Priority Data
Sep. 25, 2019  (EP) .................................... 19199673

(51) Int. Cl.
*C07C 29/60*     (2006.01)
*C07C 29/132*    (2006.01)
*C08H 8/00*      (2010.01)

(52) U.S. Cl.
CPC ............ *C07C 29/60* (2013.01); *C07C 29/132* (2013.01); *C08H 8/00* (2013.01)

(58) Field of Classification Search
CPC .. C07C 29/60; C07C 29/132–145; C08H 8/00
See application file for complete search history.

(56) References Cited

U.S. PATENT DOCUMENTS

| 4,409,032 A | 10/1983 | Paszner et al. |
| 4,461,648 A | 7/1984  | Foody |

(Continued)

FOREIGN PATENT DOCUMENTS

| WO | 9726403 A1    | 7/1997 |
| WO | 2007009463 A2 | 1/2007 |

(Continued)

OTHER PUBLICATIONS

International Search Report and Written Opinion received for PCT Patent Application No. PCT/EP2020/077009, mailed on Dec. 18, 2020, 10 pages.

(Continued)

*Primary Examiner* — Medhanit W Bahta
(74) *Attorney, Agent, or Firm* — Shell USA, INC.

(57) ABSTRACT

A process for the preparing glycols from a lignocellulosic solid biomass involves contacting the biomass with an organic solvent comprising a low boiling point alcohol and a pre-treatment acid at a temperature in a range from 80 to 220° C. and a pressure in a range from 1 to 50 bara. The resulting mixture, having >20 wt. % water, is separated into a pre-treated solid residue comprising cellulose and a liquid stream comprising dissolved lignin and hemicellulose. The pre-treated solid residue is subjected to a hydrogenolysis reaction, generating a glycols stream, a lights stream, comprising a first portion of organic solvent, and a heavies stream. At least of part of the liquid stream is separated to (Continued)

produce a second portion of organic solvent and a solid residue of lignin and hemicellulose. At least part of the first and second portion of organic solvent is recycled to the contacting step.

14 Claims, 2 Drawing Sheets

(56) References Cited

U.S. PATENT DOCUMENTS

| | | | |
|---|---|---|---|
| 10,087,160 B2 | 10/2018 | Chheda et al. | |
| 2008/0064906 A1 | 3/2008 | Foody et al. | |
| 2019/0144409 A1 | 5/2019 | Chheda et al. | |
| 2022/0356134 A1* | 11/2022 | McKay | C07C 29/132 |

FOREIGN PATENT DOCUMENTS

| | | |
|---|---|---|
| WO | 2010121366 A1 | 10/2010 |
| WO | 2017070067 A1 | 4/2017 |

OTHER PUBLICATIONS

Fabicovicova et al., "From Barley Straw to Valuable Polyols: A Sustainable Process Using Ethanol/Water Mixtures and Hydrogenolysis over Ruthenium-tungsten Catalyst", Chemsuschem, vol. 9, Issue No. 19, Aug. 25, 2016, pp. 2804-2815, XP055452942.

Brosse et al., "Pretreatment of Miscanthus X Giganteus Using the Ethanol Organosolv Process for Ethanol Production", Industrial & Engineering Chemistry Research, vol. 48, Issue No. 18, Sep. 16, 2009, pp. 8328-8334, XP055262324.

Mosier et al., "Features of Promising Technologies for Pretreatment of Lignocellulosic Biomass" Bioresource Technology, vol. 96, Issue No. 6, Apr. 2005, pp. 673-686.

Holtzapple et al., "The Ammonia Freeze Explosion (AFEX) process", Applied Biochemistry and Biotechnology, vol. 28/29, 1991, pp. 59-74.

Kumar et al., "Methods for Pretreatment of Lignocellulosic Biomass for Efficient Hydrolysis and Biofuel Production", Industrial & Engineering Chemistry Research. vol. 48, Issue No. 8, Mar. 20, 2009, pp. 3713-3729, XP002670851.

Lavarack et al., "The Acid Hydrolysis of Sugarcane Bagasse Hemicellulose to Produce Xylose,Arabinose,Glucose and Other Products", Biomass and Bioenergy, vol. 23, May 17, 2002, pp. 367-380.

Lynd et al., "Microbial Cellulose Utilization: Fundamentals and Biotechnology", Microbiology and Molecular Biology Reviews, vol. 66, Issue No. 3, Sep. 2002, pp. 506-577.

International Search Report and Written Opinion received for PCT Patent Application No. PCT/EP2020/077013, mailed on Dec. 18, 2020, 10 pages.

* cited by examiner

PRE-TREATMENT OF LIGNOCELLULOSIC FEEDS FOR THE PRODUCTION OF GLYCOLS

CROSS REFERENCE TO RELATED APPLICATIONS

This is a National stage application of International application No PCT/EP2020/077009, filed Sep. 25, 2020, which claims priority of European application No. 19199673.5, filed 25 Sep. 2019 which is incorporated herein by reference in its entirety.

TECHNICAL FIELD

The present invention relates to a process for converting a lignocellulosic feed stock into glycols. More specifically, the present invention relates to an integrated process for the pre-treatment of a lignocellulose to deliver a cellulosic residue that has a reduced amount of lignin which may be fed to a hydrogenolysis process.

BACKGROUND

Ethylene glycol and propylene glycol are valuable materials with a multitude of commercial applications, e.g. as heat transfer media, antifreeze, and precursors to polymers, such as PET. Ethylene and propylene glycols are typically made on an industrial scale by hydrolysis of the corresponding alkylene oxides, which are the oxidation products of ethylene and propylene, produced from fossil fuels.

In recent years, increased efforts have focused on producing chemicals, including glycols, from renewable feedstocks, such as plant and/or sugar-based materials. The conversion of sugars to glycols can be seen as an efficient use of the starting materials with the oxygen atoms remaining intact in the desired product.

Lignocellulosic solid biomass is viewed as an abundant renewable resource for chemicals due to the presence of sugars in the cell walls of plants. More than 50% of the organic carbon on the earth's surface is contained in plants. Lignocellulosic solid biomass is comprised of hemicelluloses, cellulose and smaller portions of lignin and protein. These structural components are comprised primarily of pentose and hexose sugar monomers. Cellulose is a polymer comprised mostly of condensation polymerized glucose and hemicellulose is a polymer that consists of a variety of hexose and/or pentose sugars, for example mostly xylose. These sugars can be converted into valuable components, provided they can be liberated from the cell walls and polymers that contain them. However, plant cell walls have evolved considerable resistance to microbial, mechanical or chemical breakdown to yield component sugars. In order to overcome recalcitrance, ground biomass is altered by a variety of processes known as pretreatment. The aim of the pretreatment is to hydrolyze the hemicellulose, break down the protective lignin structure and disrupt the crystalline structure of cellulose. All of these steps enhance accessibility to the cellulose during the subsequent hydrolysis (saccharification) step.

Organosolv pretreatment removes all or a portion of lignin upstream of downstream processes. This pretreatment involves the addition of organic solvents, such as ethanol, to lignocellulosic feedstock to extract the lignin.

For the production of cellulose in pulp and paper production, cellulosic biomass can be heated in a solvent comprising formic acid. In WO-A-97/26403 for example, a process is described for producing pulp from reed canary grass by subjecting the grass to a formic acid cooking step, optionally followed by a bleaching step.

The saccharification of the cellulose holds promise of greater yields of sugars under milder conditions and is therefore considered by many to be more economically attractive. The recalcitrance of the raw biomass to hydrolysis necessitates a pretreatment to enhance the susceptibility of the cellulose to hydrolytic catalysts. A number of pretreatment methods, such as described by Mosier, et al. [*Bioresource Technology*, Vol. 96, pp. 673-686 (2005)], have been developed to alter the structural and chemical composition of biomass to improve conversion. Such methods include treatment with a dilute acid steam explosion, as described in U.S. Pat. No. 4,461,648, hydrothermal pretreatment without the addition of chemicals as described in WO 2007/009463 A2, ammonia freeze explosion process as described by Holtzapple, M. T., et al. [*Applied Biochemistry and* Biotechnology, 28/29, pp. 59-74], and an organosolv extraction process described in U.S. Pat. No. 4,409,032. Despite these approaches, such pretreatment has been cited as the most expensive process in biomass-to-fuels conversion [*Ind. Eng. Chem. Res.*, Vol. 48(8), 3713-3729 (2009)].

One pretreatment that has been extensively explored is a high temperature, dilute-sulfuric acid ($H_2SO_4$) process, which effectively hydrolyzes the hemicellulosic portion of the biomass to soluble sugars and exposes the cellulose so that saccharification is successful. The parameters which can be employed to control the conditions of the pretreatment are time, temperature, and acid loading. These are often combined in a mathematical equation termed the combined severity factor. In general, the higher the acid loading employed, the lower the temperature or the shorter the reaction time that can be employed; this comes at the cost of acid and a need to recycle the acid. Conversely, the lower the temperature, the longer the pretreatment process takes; this comes at the cost of productivity. However, the use of the higher concentrations of acid requires lowering the pretreatment temperatures below that where furfural formation becomes facile [B. P. Lavarack, et al., *Biomass and Bioenergy*, Vol. 23, pp. 367-380 (2002)] once again requiring the recovery of the strong acid. If dilute acid streams and higher temperatures are employed in the pretreatment reaction, the acid passing downstream to the hydrolysis and subsequent fermentation steps must be neutralized resulting in inorganic salts which complicates downstream processing and requires more expensive waste water treatment systems. This also results in increased chemical costs for acid and base consumption.

These pretreatments have generally been designed to provide pulp or enable hydrolysis and fermentation of the cellulosic sugars. However, these pretreatments may impact sugar hydrogenolysis processes which have specific characteristics and sensitivities. For example, sugar hydrogenolysis uses a metal catalyst that is sensitive to electronegative elements, such as sulfur, chlorine and possibly nitrogen typically found in lignocellulosic feedstock. Sugar hydrogenolysis also operates at various pH and are therefore sensitive to acidic and basic impurities present in the lignocellulosic feedstock or provided by the pretreatment.

Katarina Fabicovicova et al. "From Barley 1,2,4-15 Straw to Valuable Polyols: A Sustainable Process Using Ethanol/Water Mixtures and Hydrogenolysis over Ruthenium-Tungsten Catalyst", ChemSusChem, vol. 9, pages 2804-2815, 2016, discloses a process in which a lignocellulosic feedstock was pre-treated with ethanol/water mixtures. The content of lignin in the biomass decreased for most samples.

The influence of water on hemicellulose liquefaction was also studied. After the pre-treatment the biomass material was subjected to hydrogenolysis over a Ru-W/AC catalyst. The formation of undesired side-products is discussed in this article.

Therefore, it would be advantageous to provide an improved pre-treatment method for the production of glycols from lignocellulosic feedstock to reduce lignin, amino acids and ash.

SUMMARY

Accordingly, the present invention provides a process for the preparation of glycols from a lignocellulosic solid biomass comprising cellulose, hemicellulose and lignin in a reactor system, said process including: a) contacting the lignocellulosic solid biomass with an organic solvent comprising a low boiling point alcohol and a pre-treatment acid at a temperature ranging from about 80 to about 220° C. and a pressure ranging from 1 to 50 bar (absolute) for a time ranging from about 5 minutes to about 2 hours to obtain a first mixture; b) separating the first mixture obtained in step (a) into a pre-treated solid residue comprising cellulose and a liquid stream comprising dissolved lignin and hemicellulose; c) subjecting the pre-treated solid residue to a hydrogenolysis reaction and generating a glycols stream, a lights stream and a heavies stream; d) recycling at least a part of the lights stream to step (a), wherein the lights stream comprises a first portion of the organic solvent; e) separating at least of part of the liquid stream from step b) to produce a second portion of the organic solvent and a solid residue that comprises lignin and hemicellulose; and f) recycling at least a part of the second portion of the organic to step (a), wherein the first mixture has greater than about 20 wt % water, wherein the pre-treatment acid comprises at least one selected from the group consisting of formic acid, acetic acid, propionic acid, butyric acid, glycolic acid, lactic acid, and combinations thereof which is/are at least partially generated in-situ in step (a); and wherein at least a part of the pre-treatment acid is recycled to step (a).

Additional features, advantages, and embodiments of the disclosed subject matter may be set forth or apparent from consideration of the following detailed description, drawings, and claims. Moreover, it is to be understood that both the foregoing summary and the following detailed description are examples and are intended to provide further explanation without limiting the scope of the claims.

BRIEF DESCRIPTION OF THE DRAWINGS

The accompanying drawing, which is included to provide a further understanding of the disclosed subject matter, is incorporated in and constitutes a part of this specification. The drawing also illustrates embodiments of the disclosed subject matter and together with the detailed description serves to explain the principles of embodiments of the disclosed subject matter. No attempt is made to show structural details in more detail than may be necessary for a fundamental understanding of the disclosed subject matter and various ways in which it may be practiced.

DETAILED DESCRIPTION

Figure 1:
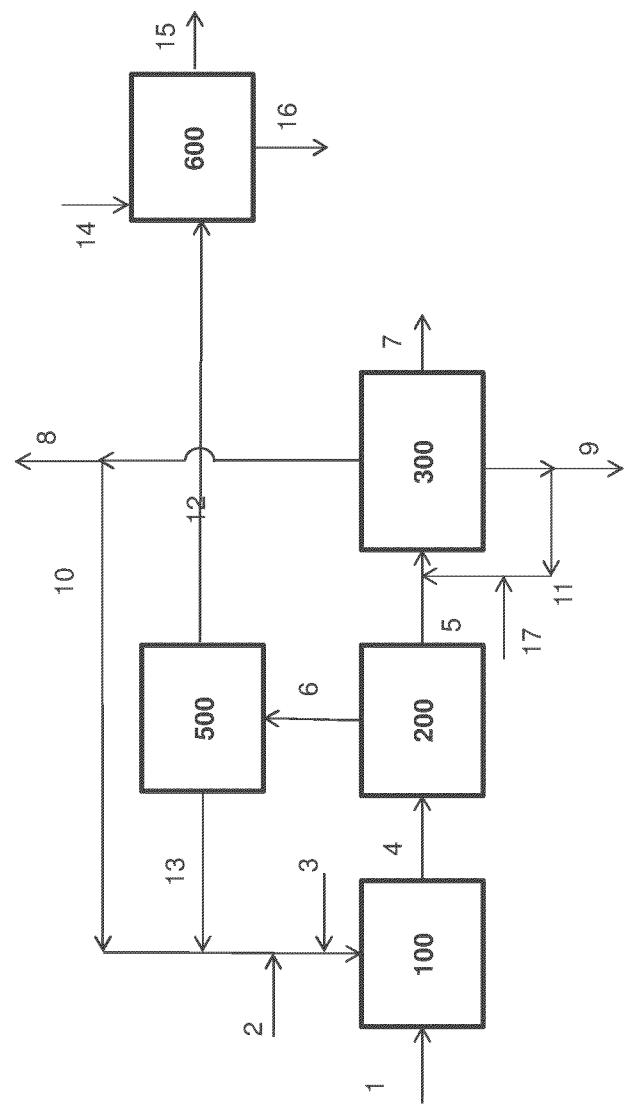
FIG. 1 shows a block flow process scheme according to an embodiment of the disclosed subject matter.

The following description of the variations is merely illustrative in nature and is in no way intended to limit the scope of the disclosure, its application, or uses. The description and examples are presented herein solely for the purposes of illustrating the various embodiments of the disclosure and should not be construed as a limitation to the scope and applicability of the disclosure.

The terminology and phraseology used herein is for descriptive purposes and should not be construed as limiting in scope. Language such as "including," "comprising," "having," "containing," or "involving," and variations thereof, is intended to be broad and encompass the subject matter listed thereafter, equivalents, and additional subject matter not recited.

Also, as used herein any references to "one embodiment" or "an embodiment" means that a particular element, feature, structure, or characteristic described in connection with the embodiment is included in at least one embodiment. The appearances of the phrase "in one embodiment" in various places in the specification are not necessarily referring to the same embodiment.

It has now been found that a solid lignocellulosic solid biomass can be treated by contacting it with an organic solvent and water at a temperature ranging from about 80 to about 220° C. to provide a pre-treated solid residue which is subjected to hydrogenolysis reaction generating a glycols stream.

The treatment (or pre-treatment) may be included in a process for the preparation of glycols from a lignocellulosic solid biomass comprising cellulose, hemicellulose and lignin in a reactor system, said process including (a) contacting the lignocellulosic solid biomass with an organic solvent comprising a low boiling point alcohol and a pre-treatment acid at a temperature ranging from about 80 to about 220° C. and a pressure ranging from 1 to 50 bar (absolute) for a time ranging from about 5 minutes to about 2 hours to obtain a first mixture; (b) separating the first mixture obtained in step (a) into a pre-treated solid residue comprising cellulose and a liquid stream comprising dissolved lignin and hemicellulose; (c) subjecting the pre-treated solid residue to a hydrogenolysis reaction and generating a glycols stream, a lights stream and a heavies stream; (d) recycling at least a part of the lights stream to step (a), wherein the lights stream comprises a first portion of the organic solvent; (e) separating at least of part of the liquid stream from step b) to produce a second portion of the organic solvent and a solid residue that comprises lignin and hemicellulose; and (f) recycling at least a part of the second portion of the organic to step (a), wherein the first mixture has greater than about 20 wt % water, wherein the pre-treatment acid comprises at least one selected from the group consisting of formic acid, acetic acid, propionic acid, butyric acid, glycolic acid, lactic acid, and combinations thereof which is/are at least partially generated in-situ in step (a); and wherein at least a part of the pre-treatment acid is recycled to step (a).

The pre-treatment acid comprises at least one selected from the group consisting of formic acid, acetic acid, propionic acid, butyric acid, glycolic acid, lactic acid, and combinations thereof which is/are at least partially generated in-situ in step (a). At least a part of the pre-treatment acid is recycled to step (a). The pre-treatment acid may be recovered from one or more solid and/or one or more liquid streams of the process. Recovery may be performed by means of washing, drying, heating, reducing pressure, electrodialysis, membrane separation, reversed osmosis, or combinations thereof.

The process advantageously produces cellulose suitable for hydrolysis into sugars, which in turn can be processed into glycols.

The process according to an embodiment allows the separation of lignocellulose into cellulose, hemi-cellulose (and its breakdown products) and high quality lignin. In particular, the lignin and hemicellulose are separated from the cellulose and then further treated to produce depolymerized lignin and an aqueous hemicellulose stream. The depolymerized lignin may be employed to form thermosetting resin products with carbonyl compounds such as formaldehyde, through the phenolic hydroxyl-groups and active sites on the aromatic ring. The hemicellulose may be employed to form furfural.

The present process thus not only converts the cellulose and hemicellulose into valuable intermediates or final products, but also produces lignin which can be employed as a chemical intermediate rather than as fuel only.

Pre-treatment: In step (a), a lignocellulosic solid biomass is contacted with an organic solvent and a pre-treatment acid to obtain a first mixture. The first mixture may include a pre-treated solid residue and a liquid. The first mixture may be termed a "pulping slurry." The contacting of step (a) may be done in any reactor or other means suitable for the reaction and capable of operating under the conditions of step (a). The organic solvent comprises water and a low boiling point alcohol. The low boiling point alcohol preferably comprises at least one selected from the group of methanol, ethanol, iso-propanol, n-propanol, and combinations thereof. During step (a) the pH of the lignocellulosic solid biomass, the organic solvent, and the pre-treatment acid solution preferably is maintained in the range from about 2 to about 6. The pH of the obtained first mixture in step (a) preferably is in the range from about 2 to about 6.

Pretreatment step (a) may be carried out in any reactor configuration suitable for solid-liquid contact, for example a co-current, counter-current of flow-through configuration. The conditions in the reactor include a temperature in the range of from about 80 to about 220° C., preferably of from about 100 to about 170° C., more preferably of from about 105 to about 150° C. Preferably, pretreatment step (a) is carried out at a pressure in the range of from about 1 to about 50 bar, preferably of from about 2 to about 25 bar, more preferably of from about 3 to about 10 bar. Pre-treatment at atmospheric pressure is particularly preferred.

In some embodiments, the organic solvent may also include a pre-treatment acid of at least one of an organic acid, an inorganic acid, or mixtures thereof. The organic acid may be at least one selected from the group consisting of α-hydroxysulfonic acids, formic acid, acetic acid, propionic acid, butyric acid, glycolic acid, lactic acid, citric acid, benzoic acid, and combinations thereof. The inorganic acid may be selected from the group consisting of hydrochloric acid, sulfuric acid, boric acid, nitric acid, phosphoric acid and mixtures thereof.

The lignocellulosic solid biomass will be contacted with the organic solvent and the pre-treatment acid for a time period sufficient to achieve at least partial hemicellulose hydrolysis and/or partial delignification, typically in the range of from about 0.5 to about 10 hours, preferably in the range of from about 5 minutes to about 2 hours. In other embodiments, the time may be greater than about 10 minutes, greater than about 30 minutes, greater than about 60 minutes or less than about 3 hours, less than about 2 hours or less than about 1 hour.

The lignocellulosic solid biomass-to-the organic solvent and pre-treatment acid ratios both should preferably be in the range of from about 1:3 to about 1:50, preferably of from about 1:5 to about 1:20. In some embodiments, the pulping slurry also includes water. The lignocellulosic solid biomass will contain water due to the moisture therein. In other embodiments, the pulping slurry may also optionally include recycled liquid stream(s) obtained from step (c) and/or (e). The pulping solution may further contain organic compounds known to be suitable organic solutions for organosolv processes. Examples of such solvents may include methanol, ethanol, iso-propanol, n-propanol acetone as well as esters such as methyl acetate, ethyl acetate, n-propyl acetate and isopropyl acetate.

In some embodiments, the organic solvent has a moisture content less than about 90 wt %, less than about 75 wt %, and less than about 50 wt %. In other embodiments, the organic solvent has a moisture content greater than 0 wt %, greater than about 15 wt %, and greater than about 30 wt %. In some embodiments, the pulping slurry has a ratio of at least about 1:1 of organic solvent to water. In other embodiments, the pulping slurry has a mass ratio of at least about 2:1 of organic solvent to water. In some embodiments, the pulping slurry has a mass ratio of at least about 3:1 of organic solvent to water. The pulping slurry contains less than about 20 wt %, more preferably less than about 10 wt % of acid components. The pulping slurry contains greater than about 20 wt %, preferably greater than about 30 wt %, and more preferably greater than about 45 wt % of water. The pulping slurry preferably contains less than about 75 wt % water.

Any suitable lignocellulosic solid biomass may be used in embodiments of the process according to the invention. Examples of suitable biomass are agricultural wastes such as corn stover, soybean stover, corn cobs, rice straw, rice hulls, oat hulls, corn fibre, cereal straw like wheat, barley, rye, and oat straw; grasses such as switch grass, miscanthus, cord grass, rye grass, reed canary grass; forestry biomass such as wood and saw dust; recycled paper or pulp fibres; sugar processing residues such as bagasse and beet pulp. Cereal straw, especially wheat straw, is particularly preferred. Prior to step (a), the solid biomass is typically comminuted into pieces or particles of a small size, preferably pieces or particles with an average length of less than about 3 cm, more preferably an average length in the range of from about 0.5 to about 2.5 cm.

In pre-treatment step (a), at least part of the hemicellulose is hydrolyzed and removed from the solid biomass. Also, part of the lignin is removed from the solid biomass. Thus, the cellulose is made more accessible for subsequent hydrolysis thus improving its digestibility. While not wishing to be bound by any theory, a minimum amount of water hydrolyzes the carbohydrate-lignin bonds and solubilizes the basic ash. The organic solvent solubilizes hemicellulose, lignin and amino acids. In a preferred embodiment, the organic solvent is a light co-product of a subsequent hydrogenolysis reaction, e.g. ethanol or propanol. In some embodiments, the pre-treatment acid acts as a catalyst and may be generated in-situ. The pre-treatment acid may be a carboxylic acid such as, but not limited to, acetic acid. The pre-treatment acid may be recovered from the pre-treated solid residue by heating and/or reducing the pressure to produce an acid-removed pre-treated solid residue and the liquid stream. The pre-treatment acid removed from the pre-treated solid residue may then be recycled to step (a). The pre-treatment acid may be recycled to step (a) along with at least a part of the lights stream.

In a preferred embodiment the pre-treatment acid comprises at least one selected from the group consisting of formic acid, acetic acid, propionic acid, butyric acid, glycolic acid, lactic acid, and combinations thereof which is/are at least partially generated in-situ in step (a).

In some embodiments, the pre-treatment acid may also include an organic acid, an inorganic acid, or mixtures thereof. The organic acid may be at least one selected from the group consisting of α-hydroxysulfonic acids, formic acid, acetic acid, propionic acid, butyric acid, glycolic acid, lactic acid, citric acid, benzoic acid, and combinations thereof. The inorganic acid may be selected from the group consisting of hydrochloric acid, sulfuric acid, boric acid, nitric acid, phosphoric acid and mixtures thereof.

The pulping slurry contains less than about 20 wt %, more preferably less than about 10 wt % of acid components. If the pre-treatment acid is a strong acid such as, but not limited to, sulfuric acid, the pulping solution may contain 0 wt %, greater than about 0.1 wt % and less than about 5 wt %, less than about 1 wt %, or less than about 0.5 wt % acid. If the pre-treatment acid is a weak acid such as, but not limited to, acetic acid, the pulping solution may contain 0 wt %, greater than about 1 wt %, greater than wt %, greater than about 10 wt % and less than about 50 wt %, less than about 35 wt %, or less than about 20 wt % acid. In a preferred embodiment, the pre-treatment acid does not include non-volatile inorganic acids but only volatile organic acids, which may facilitate the cleaning of the lignin by evaporation. In other embodiments, if the lignin contains non-volatile acids and/or sugars, the lignin will need a water wash and a drying step, e.g. after solvent evaporation. As used in this description, strong acids have a pKa<−1.74. An example of a strong acid is hydrochloric acid (HCl), whose pKa is −6.3.

Solid recovery and wash: In step (b), the first mixture obtained in step (a) is separated into a pre-treated solid residue including cellulose and a liquid stream including dissolved lignin and hemicellulose. This separation can be carried out by any suitable technique known in the art, for example filtration or centrifugation. The separation in step (b) preferably is performed by pressing the mixture in a suitable press filter, screw press, rotary drum or any other means suitable to separate a solid/liquid mixture that is highly corrosive and highly viscous at the reaction conditions. Examples for suitable means include conveyer belts, screw presses, extruders, centrifuges. Preferably a screw press is used. In some embodiments, the liquid stream includes lignin, ash and acid. In some embodiments, the liquid stream is recycled to step (a). This liquid stream may be recycled with or without any further processing.

Steps (a) and (b) may be integrated, preferably when operating the process continuously. Both steps may happen simultaneously, e.g. in a screw press. The liquid stream(s) obtained in step (b) may be referred to herein as black liquor.

In some embodiments, the pre-treated solid residue may be sent to step c) without washing and/or drying. However, in other embodiments, in order to remove remaining organic solvent, pre-treatment acid and lignin/hemicellulose from the pre-treated solid residue, step (b) may further comprise one or more optional washing steps with a washing liquid such as water, acetic acid, the organic solvent, the pre-treatment acid, or an otherwise suitable aqueous stream, such as a recycle stream obtained from step (c) and/or (e) stream, to remove residual hemi-cellulose and lignin from the pre-treated solid residue. In some embodiments, the washing liquid may be a combination of water and the aqueous recycle from steps (c) and/or (e) may be used. In another embodiment, the pre-treated solid residue is washed with a fresh medium comprising acetic acid. The washing step occurs in a counter flow or cross flow manner In some embodiments, the washing liquid is compatible with components of the hydrogenolysis step which follows.

The washing liquid preferably comprises less than 50 vol % water, preferably less than 40 vol % water. In order to improve lignin removal, the washing liquid may further comprise acetic acid. Pure water or acetic acid/water mixtures are particularly suitable washing liquids. More than one washing steps may be carried out, for example a first washing step with an acetic acid/water mixture followed by one or more washing steps with water only or several washing steps with water only. The washing step(s) may be typically carried out at a temperature in the range of from ambient to about 100° C., preferably of from about 20 to about 90° C.

After each or all of the optional washing step(s), the obtained mixture may be separated into a liquid stream and washed pre-treated solid residue. The liquid stream, including dissolved and hydrolyzed hemicelluloses, lignin, residual organic solvent and pre-treatment acid from the pre-treated solid residue may be sent for further processing in step (e) or may be recycled in part to step (a).

In some embodiments, step (b) may optionally further contain a second step wherein the liquid content of the pre-treated solid residue is further reduced. After the pre-treated solid residue is separated from the liquid stream, the pre-treated solid residue typically has a solids content of about 50 wt %. However, in order to increase the effectiveness of further processing, the solids content preferably is increased to at least 65 wt %, preferably more than 65 wt %, more preferably at least 70 wt % This is preferably done by the use of an air blower or dryer.

Hydrogenolysis: The pre-treated solid residue obtained in step (b) is next subjected to a hydrogenolysis reaction in step (c). The hydrogenolysis reaction includes contacting the pre-treated solid residue, a soluble retro-Aldol catalyst, and optionally a hydrogenolysis acid in a reactor under hydrogenation conditions, with a heterogeneous hydrogenation catalyst. Product streams from the hydrogenolysis reaction include a glycols stream, a lights stream and a heavies stream may be obtained from the reactor.

The hydrogenolysis acid may be one of a low-molecular weight organic acid, a carbonic acid, a mineral acid, and combinations thereof. The low-molecular weight organic acid may be at least one of: formic acid, acetic acid, propionic acid, butyric acid, glycolic acid, lactic acid, citric acid, benzoic acid, and combinations thereof. The mineral acid may be at least one of: sulfuric acid, phosphoric acid, boric acid, and combinations thereof. In some embodiments, the pre-treatment acid and hydrogenolysis acid are the same.

The soluble retro-Aldol catalyst may comprise one or more compounds, complex or elemental material comprising tungsten, molybdenum, vanadium, niobium, chromium, titanium or zirconium. In particular, the soluble retro-Aldol catalyst may comprise one or more materials selected from the list consisting of tungstic acid, molybdic acid, ammonium tungstate, ammonium metatungstate, ammonium paratungstate, tungstate compounds comprising at least one Group I or II element, metatungstate compounds comprising at least one Group I or II element, paratungstate compounds comprising at least one Group I or II element, heteropoly compounds of tungsten, heteropoly compounds of molybdenum, tungsten oxides, molybdenum oxides, vanadium oxides, metavanadates, chromium oxides, chromium sulfate, titanium ethoxide, zirconium acetate, zirconium carbonate, zirconium hydroxide, niobium oxides, niobium ethoxide, and combinations thereof. The metal component is in a form other than a carbide, nitride, or phosphide. According to an embodiment, examples of the soluble retro-Aldol catalyst may include at least one of: silver tungstate, sodium tungstate, sodium meta-tungstate, ammonium meta-tungstate, sodium poly-tungstate, tungstic acid, alkali- and alkaline-earth metal tungstates, sodium phospho-tungstate, phospho-tungstic acid, alkali- and alkaline-earth metal phospho-tungstates, alkali- and alkaline-earth metal molybdates, alkali- and alkaline-earth metal phospho-molybdates, phospho-molybdic acid, heteropoly acids, mixed tungstates and molybdates, niobic acid, silicotungstic acid, alkali- and alkaline-earth metal niobates. In an aspect, the soluble retro-Aldol catalyst may be sodium tungstate.

In some embodiments, heterogeneous hydrogenation catalysts may be supported or un-supported metal catalysts selected from Group 8 to Group 11 metals in the periodic table. Examples of un-supported metal catalysts are Raney-metal catalysts such as Raney-Ni, Raney-Co, Raney-Cu, and Raney-Ru, and metal-powder catalysts such as powdered Ni, Co, Cu, Cu—Zn, Cu—Cr, Ni—Mo, Ni—W, and Ni—Cr. The heterogeneous hydrogenation catalyst may be promoted with metals such as Al, Fe, Cr, Mn, Co, Cu, Mo, Ru, Rh, Pd, Ag, W, Re, Ir, Pt, Au, In, Sn, Sb, and Pb. One or more metals may be used in the formulation of the promoted metal catalysts. The promoting metals may be present in concentrations ranging from about 0.001 wt % to about 10 wt %. Examples of supported-metal hydrogenation catalysts are Group 8 to Group 11 metal catalysts supported on hydrothermally stable supports such as $TiO_2$, $ZrO_2$, and alpha-alumina. The metals may be used individually or in combination with one or more of the other metals.

According to an embodiment, at least one of the heterogeneous hydrogenation catalyst and soluble retro-Aldol catalyst is supported on a solid support. In an embodiment, any other active catalyst component may be present in either heterogeneous or homogeneous form. In this case, any other active catalyst component may also be supported on a solid support. In one embodiment, the heterogeneous hydrogenation catalyst is supported on one solid support and the soluble retro-Aldol catalyst is supported on a second solid support which may comprise the same or different material. As a specific example, the heterogeneous hydrogenation catalyst may be a hydrogenation catalyst supported on a hydrothermally stable support. In another embodiment, both the heterogeneous hydrogenation catalyst and soluble retro-Aldol catalyst are supported on one solid hydrothermally stable support.

The solid support may be in the form of a powder or in the form of regular or irregular shapes such as spheres, extrudates, pills, pellets, tablets, monolithic structures. Alternatively, the solid supports may be present as surface coatings, for examples on the surfaces of tubes or heat exchangers. Suitable solid support materials are those known to the skilled person and include, but are not limited to aluminas, silicas, zirconium oxide, magnesium oxide, zinc oxide, titanium oxide, carbon, activated carbon, zeolites, clays, silica alumina and mixtures thereof.

In some embodiments, the hydrogenolysis reaction may also include a reaction solvent. The reaction solvent may be water, a C1 to C6 alcohol, a C1 to C6 polyol, or mixtures thereof. Further reaction solvents may also be added to the reactor in a separate feed stream or may be added to the carbohydrate feed before it enters the reactor. Examples of C1 to C6 polyols include 1,2-hexanediol, glycerol, etc. As an example, the reaction solvent may be a mixture including water and at least one of alcohols, ethers, and ether-alcohols, and mixtures thereof. In an embodiment, the reaction solvent may be water.

Step (c) may be performed under hydrogenation conditions to maximize the desired yield of glycols. For example, the hydrogenation conditions may include temperature, pressure, flow rate, and any other process variable that may be controlled. In an embodiment, the hydrogenation conditions may include a temperature in the range of from about 180 to about 250° C. and from about 200 to about 250° C. The hydrogenation conditions may also include a pressure in the range of from about 35 to about 140 bar. The residence time in the hydrogenation reactor vessel of may be at least about 1 minute, at least about 2 minutes, and at least about 5 minutes. Suitably the residence time in the hydrogenation reactor vessel is no more than about 5 hours, no more than about 2 hours, and no more than about 1 hour. According to an implementation, the average residence time in the hydrogenation reactor vessel is no more than about 2 hours.

In an embodiment, step (c) may also include contacting the pre-treated solid residue with hydrogen. Hydrogen may be supplied into the reactor vessel under pressure in a manner common in the art. In an example, the method of step (c) takes place in the absence of air or oxygen. In order to achieve this, it is preferable that the atmosphere in the reactor vessel be evacuated and replaced with hydrogen repeatedly, after loading of any initial reactor vessel contents, and before the reaction starts.

In some embodiments, prior to the pre-treated solid residue obtained in step (b) entering the hydrogenolysis reaction in step (c), the pre-treated solid residue may be subjected to enzymatic hydrolysis. The enzymatic hydrolysis transforms some of the cellulose in the pre-treated solid residue into glucose which is fed into the hydrogenolysis reaction. The cellulose in the pre-treated solid residue may be more accessible and thus may improve its enzymatic digestibility. Suitable enzymes and process conditions for enzymatic hydrolysis are known in the art, for example from WO2006/034590 or Lynd et al., Microbial Cellulose Utilization: Fundamentals and Biotechnology, Microbiology and Molecular Biology Reviews, 66 (2002), p 506-577.

According to the presently disclosed subject matter, multiple product streams may be obtained from step (c) including a glycols stream, a lights stream and a heavies stream. The separation of the product streams is known to one skilled in the art. The glycols stream may include at least about 5 wt % concentration of glycols. In addition, the glycols stream may represent a yield from saccharides of at least about 60 wt % glycols, and at least about 70 wt % glycols. In an embodiment, the glycols stream may represent a yield from saccharides of at least about 60 wt % ethylene glycol, and at least about 65 wt % ethylene glycol. An advantage of the presently disclosed method is the ability to maximize the yield of ethylene glycol relative to the yield of propylene glycol. For example, the glycols stream may include an ethylene glycol/propylene glycol wt % yield ratio of at least about 1:1, an ethylene glycol/propylene glycol wt % yield ratio of at least about 7:1, and an ethylene glycol/propylene glycol wt % yield ratio of at least about 10:1. In addition, the presently disclosed method allows for minimizing undesired products of the subject reaction. Accordingly, the glycols stream may include a yield of no more than about 10 wt % sorbitol. Further, the glycols stream may include a yield of less than about 3 wt % 1,2-butanediol. Additionally, the glycols stream may include a minimum ethylene glycol/1,2-butanediol wt % yield ratio of about 20:1, thereby maximizing the ethylene glycol yield relative to other less desired products.

According to an embodiment, the glycols stream may be further processed. For example, the glycols stream may be fed to a second reactor for contacting with hydrogen in the presence of a heterogeneous hydrogenation catalyst. A final product stream comprising ethylene glycol may be obtained that is substantially free of compounds containing carbonyl functional groups. The heterogeneous hydrogenation catalyst used in this further processing of the glycols stream may or may not be the same heterogeneous hydrogenation catalyst used in the bi-functional catalyst system in the glycols production process.

Recycle: In some embodiments, after the hydrogenolysis reaction in step (c), at least a portion of the lights stream is recycled to step (a) for contacting with the lignocellulosic solid biomass in step (d). The lights stream may include a first portion of the organic solvent. In some embodiments, the lights stream may also include a portion of the pre-treatment acid. In some embodiments, the organic solvent is a by-product from the hydrogenolysis reaction. Thus, the first portion of the organic solvent supplements the organic solvent initially added in step (a).

In some embodiments, after the hydrogenolysis reaction in step (c), at least a portion of the heavies stream is recycled back to step (c). In some embodiments, the heavies stream includes the retro-Aldol catalyst. Thus, the portion of the heavies stream supplements the retro-Aldol catalyst initially added in step (c). In some embodiments, the heavies stream includes the hydrogenolysis acid. Thus, the portion of the heavies stream supplements the hydrogenolysis acid initially added in step (c).

In some embodiments, the process also includes separating at least of part of the liquid stream from step b) to produce a second portion of the organic solvent and a solid residue that comprises lignin and hemicellulose in step (e). The separation in step (e) preferably is performed by heating the liquid stream to a temperature ranging from about 50° C. to about 150° C. The separation in step (e) may also be performed by numerous methods known by one skilled in the art. The second portion of the organic solvent may be recycled to step (a) in step (f). In some embodiments, the second portion of the organic solvent may also include a portion of the pre-treatment acid. In some embodiments, the lignin stream includes at least about 80 wt % lignin, more preferably about 90 wt % lignin, and most preferably about 95 wt % lignin. In some embodiments, the lignin from step (e) is ready to be used without further processing, for example as a starting material for thermosetting resins.

In some cases, the solid residue is washed with water to solubilize the hemicellulose and leave behind a solid lignin. The aqueous hemicellulose may be converted to furfural using a process such as that disclosed in U.S. Pat. No. 10,0870,160 and U.S. Patent Publication 20190144409, the entirety of which are hereby incorporated by reference.

In some cases, the lignin solid from step (e) may contain inorganic acid, sugars (hemicellulose) and/or ash (from the biomass). The lignin solid may be washed with water and then dried to remove these contaminants The washed lignin may be free of carbohydrates, microbial biomass (dead cells, proteins, cell membranes, etc.), inorganics (ash) and light organic solvents and is sometimes referred to as "high quality" lignin. In particular, the lignin may be employed to form thermosetting resin products with carbonyl compounds such as formaldehyde, through the phenolic hydroxyl-groups and active sites on the aromatic ring.

FIG. 1 shows an embodiment of a block flow process scheme according to an implementation of the disclosed subject matter. Lignocellulosic material 1 is placed in vessel 100. Organic solvent 2 and a pre-treatment acid 3 are also added to the vessel 100. The vessel 100 operates at temperatures ranging from about 80 to about 220° C., pressures ranging from 1 to 50 bar (absolute) for a time ranging from about 5 minutes to about 2 hours. A first mixture 4 is obtained and fed to a separator 200. The first mixture 4 is separated into a pre-treated solid residue 5 and a liquid stream 6. The pre-treated solid residue 5 is fed to reactor 300 for hydrogenolysis. The products from the reactor 300 include a glycols stream 7, a lights stream 8 and a heavies stream 9. A portion 10 of the lights stream 8 may be recycled back to vessel 100. The portion 10 of the lights stream may include a portion of organic solvent and a portion of the pre-treatment acid, which supplement the organic solvent 2 and the pre-treatment acid 3 initially added to the vessel 100. A portion 11 of the heavies stream 9 may be recycled back to reactor 300. In some embodiments, an additional stream 17 is fed to the reactor 300. The additional stream 17 may comprise one or more of the retro-Aldol catalyst, the hydrogenolysis acid or a mixture of both. The heavies stream may include a portion of the hydrogenolysis catalyst. The liquid stream 6, including lignin, hemicellulose, organic solvent, ash and acid may be separated into a lignin/hemicellulose solid stream 12 and an organic solvent and acid stream 13. The organic solvent and acid stream 13 supplements the organic solvent 2 and the pre-treatment acid 3 initially added to the vessel 100. The lignin/hemicellulose solid stream 12 may be washed with water 14 to produce an aqueous hemicellulose stream 15 and a solid lignin product 16.

Examples 1-2

Embodiments of the process are designed for the use and recycle of an organic co-solvent and/or acid catalyst that may be generated from the biomass feedstock. This example demonstrates experimentally to possibility to produce glycols with good yield by pre-treating lignocellulosic biomass according to the invention.

Examples 1 and 2: Pretreatment—Biomass pretreatment was performed in a 200 mL stirred autoclave. The autoclave is equipped with a pressure sensor and two thermocouples (bottom and top of reactor respectively). The autoclave is positioned in a metal block which is equipped with cartridge heaters & copper tubing (heating & cooling by convection).

In a typical experiment the reactor was charged with 10 grams of biomass (Poplar wood, 4 wt % moisture content, sieve fraction 1-2 mm) and 90 grams of solvent. The solvent consists of mixtures of water:ethanol or water: acetic acid, as reported below. The reactor was sealed, followed by a leak test with nitrogen at ~30 bar. The autoclave was flushed with nitrogen 3 times (pressurized till 30 bar $N_2$, depressurized/$N_2$ vented, repeated 3 times). Finally, the autoclave was pressurized with 3 bar $N_2$ to ensure inert atmosphere and proper sealing of the inlet valve. The stirrer was started and the reactor was heated by the cartridge heater. After the reactor temperature (Temperature measured in the bottom/liquid phase) attained the desired reaction temperature (180° C. or 200° C., as reported below) it was kept at this desired temperature 1 to 5 hours (as reported below). After the desired reaction time the autoclave was actively cooled by means of a water cooled copper tubing.

The autoclave was opened and the slurry (solid residue and solvent) were filtered over a 5 µm wire mesh. Additional solvent was forced out of the solid cake. When no more solvent could be recovered, the solid cake was removed and dried in the fume hood for several days.

After drying the solid residue was washed with a mixture of 50/50 water/ethanol until no colour change was observed. Subsequently the solid residue was dried by nitrogen flushing until no weight change of the solid residue was observed.

Hydrogenolysis—The hydrogenolysis experiments are performed in a 45 mL autoclave. The reactor is mounted on a pneumatic arm. A preheated fluidized bed and water bath allowed for rapid heating and cooling respectively. The autoclave is equipped with a pressure transducer and a thermocouple located in the bottom of vessel. The reactor was stirred by a hollow shaft stirrer. Characteristics of the biomass feedstocks are presented in the table below.

TABLE 1

Biomass feedstocks

| | Feedstocks | |
|---|---|---|
| | Poplar Wood (after grinding) | Cellulose (Avicel PH101) |
| Particle size (pm) | <53 | ~50 |
| Saccharide content, wt % | 70 | 100 |

Typically, the reactor was charged with 14.25 g of solvent, 0.75 g of biomass, 0.02 g of retro-aldol catalyst (sodium polytungstate), 0.086 g of hydrogenation catalyst (Raney-Ni, dry basis) and 0.3 g acetic acid and some NaOH to buffer the solution to pH 3.3. Raney-Ni was thoroughly washed with demi-water until the pH became neutral. The reactor was sealed and a leak test with nitrogen at ~120 bar was performed. The autoclave was flushed with nitrogen 2 times by pressurization to 120 bar. Subsequently, the autoclave was flushed with hydrogen 2 times by pressurization with hydrogen to 60 bar. The stirrer was started (1300 rpm) and the autoclave submerged in the fluidized bed. After the reactor temperature attained the desired reaction temperature of 245° C. it was kept at this desired temperature for 2 hours. After the desired reaction time the autoclave was actively cooled by submerging it in a water bath.

When the autoclave attained room temperature it was depressurized, whereby the gas was collected in water displacement vessel. The vessel allows for direct quantification of the gas volume. The gas composition was determined by GC (at least 3 injections). Hereafter the reactor was opened, and the reactor content was transferred to a glass bottle. A sample was taken and subjected to HPLC analysis. Remaining catalyst and unconverted residue were collected in a separate bottle by flushing the reactor with demineralized water.

HPLC analysis was performed on an Agilent 1200 series (Hi-Plex-H+column) operated at 65° C. running 5 mM $H_2SO_4$ as eluent (0.6 ml min$^{-1}$). The samples were filtered (Whatman 0.2 μm filter) prior to HPLC analysis. Optionally; samples were diluted with mili-q water prior to HPLC analysis. Standards were prepared for; Ethylene glycol, propylene glycol, glycerol, 1,2 butanediol, methanol, ethanol, 1-propanol, 2-propanol, erythritol, sorbitol, mannitol.

The hydrogenolysis yields are expressed as wt % of the polysaccharides present in the biomass used as feed for the hydrogenolysis.

TABLE 2

| | Products | | | | |
|---|---|---|---|---|---|
| Example | 1 | 2 | Comp 1 | Comp 2 | Comp 3 |
| Pre-treatment conditions | | | | | |
| T (° C.) | 180 | 200 | n/a | n/a | n/a |
| time (min) | 300 | 180 | n/a | n/a | n/a |
| biomass (wt %) | 10 | 10 | n/a | n/a | n/a |
| Type | Poplar | Poplar | Poplar | Avicel | Avicel |
| Water (wt. %) | 45 | 45 | n/a | n/a | n/a |
| Ethanol (wt. %) | 0 | 45 | n/a | n/a | n/a |
| Acetic acid (wt. %) | 45 | 0 | n/a | n/a | n/a |
| Pre-treatment results | | | | | |
| Solid residue yield (wt %) | 61 | 63 | n/a | n/a | n/a |
| polysaccharide content (wt %) (100-lignin) | 89 | 94 | 76 | 100 | 100 |
| Hydrogenolysis yields (wt % on polysaccharide) | | | | | |
| Ethylene-glycol (wt. %) | 31.8 | 26.5 | 7.7 | 31.7 | 32.7 |
| Propylene-glycol (wt. %) | 7.4 | 7.7 | 11.7 | 7.1 | 5.5 |
| Sorbitol + Mannitol (wt. %) | 9.6 | 5.1 | 6.5 | 17.5 | 15.2 |
| 1.2-Butanediol (wt %) | 8.4 | 4.1 | 4.4 | 6.1 | 6.2 |
| Glycerol (wt %) | 1.6 | 2.0 | 2.4 | 1.7 | 1.4 |
| m-Erythritol (wt %) | 2.7 | 1.9 | 1.7 | 3.7 | 3.9 |
| Xylitol (wt %) | 0.7 | 1.6 | 6.0 | n.d. | 1.2 |
| Sum (wt %) | 62.1 | 48.8 | 40.4 | 67.8 | 66.1 |
| Conversion (wt %) | 68 | 66 | 77 | 78 | n.d. |

The Comparative examples 2 and 3 (Avicel) where were evaluated in duplicate show very high EG and PG yield of ~32 wt % and 5-7 wt %, respectively. In contrast, Comparative example 1 (untreated poplar) gives very low yields of EG and PG ~8 and 12 w % respectively, while the pulp obtained by pre-treatment Examples 1 and 2 (poplar) with acetic acid gives much higher yields of EG and PG, namely 26-31 and 7-8 wt %, respectively.

Examples 3-5

The following examples illustrate ways to define a target for solvent recovery to match the amount of solvent that can be produced from the biomass during the process and, thereby, avoid the need for purchasing fresh solvent. While not being bound by any theory, the purpose of the recycle is to compensate for the inevitable losses which occur during the process without importing additional co-solvent or acid. The match of the make-up to the losses may be described in the equations below:

Make up [kg/h]>losses [kg/h]

Solvent yield [g solvent/g feed]*feed concentration [g feed/g solution]>solvent lost fraction [g lost/g solvent]*solvent concentration [g solvent/g solution]

Which is identical to

Yield/lost fraction>feed concentration/solvent concentration

Example 3 (loss of alcohol solvent): The digester feed solution consists of 10 wt % biomass and 45 wt % alcohol solvent, the remaining 45 wt % being water. The hydrogenolysis of the carbohydrate yields 10 wt % in alcohol solvents (ethanol +propanol) and the carbohydrates account for 70 wt % of the biomass. Accordingly, the maximum solvent amounts to:

Solvent loss fraction <(0.1*0.7*0.1)/0.45<1.5 wt %

Consequently, >98.5 wt % of the solvent that is fed to the biomass digester will have to be recovered at some point in the process.

Example 4 (loss of acetic acid): The digester feed solution consists of 10 wt % biomass and 45 wt % acetic acid, the remaining 45 wt % being water. The digestion of the biomass yields 5 wt % of acetic acid. Accordingly, the maximum solvent amounts to:

Loss fraction <(0.05*0.1)/0.45<1.1 wt %

Consequently, >98.9 wt % of the acetic acid that is fed to the biomass digester will have to be recovered at some point in the process.

The pH of a solution of water:acetic acid in 1:1 weight ratio is very acidic and thereby suitable for biomass digestion. With a pKa of 4.76 for acetic acid, this solution can be calculated to have a pH of about 1.6.

Example 5 (loss of solvent and acetic acid): The digester feed solution consists of 10 wt % biomass, 25 wt % alcohol solvent and 20 wt % acetic acid, the remaining 45 wt % being water. The digestion of the biomass yields 5 wt % of acetic acid and the hydrogenolysis of the carbohydrate yields 10 wt % in alcohol solvents (ethanol and propanol) and the carbohydrates account for 70 wt % of the biomass. Accordingly, the maximum solvent loss amounts to:

Solvent Loss fraction <(0.1*0.7*0.1)/0.25<2.8 wt %

Acid Loss fraction <(0.05*0.1)/0.2<2.5 wt %

Consequently, >97.2 wt % of the solvent and >97.5 wt % of the acetic acid that is fed to the biomass digester will have to be recovered at some point in the process. This also means that the fraction of organic additive, i.e. solvent+acid, that needs to be recovered amounts to >(2.8%*0.25+2.5%*0.2)/(0.25+0.2)>2.7 wt %.

Examples 3-5 show stringent solvent and acid recovery targets, thereby, confirming the need for designing a process with excellent recovery potential. The experienced practitioners will know how to adjust these loss criteria for the exact configuration of the process.

Examples 6-7

The examples 6-7 propose options to further reduce the energy demand of the solvent recovery.

Example 6 (effect of biomass loading): Another parameter for the process is too achieve high biomass loading. This can be achieved directly by using a higher biomass/solvent ratio, e.g. 20 wt % compared to the 10 wt % mentioned in previous examples. The expert will recognize that, based on the equations proposed earlier, a doubling of the biomass loading will result in a doubling of the solvent loss that is acceptable. Such a doubling of the biomass loading will also result in a doubling (approximately) of the process throughput, all equipment remaining largely unaffected. This will result in a reduction of investment and energy cost per ton of biomass processed (or pulp produced) by about 50%.

Example 7 (solvent recycling prior to recovery): The above can also be achieved indirectly by recovering the solvent after L/S separation and recycling part of it directly to the digestor, with dissolved lignin and hemicellulose products, while the remaining part is sent to the work-up section to recover the solvent from the lignin and dissolved hemicellulose. This may reduce the need of clean solvent and, thereby, allow higher solvent loss. For instance, one can envisage splitting the liquid product (after L/S separation) in two equivalent fractions, one being directly recycled to the digester with lignin and cellulose, the other being send to an evaporation unit to recover the solvent, acetic acid and water (from lignin and cellulose) and recycle this purified liquid stream also the digester. Expert in the art will recognize the such a scheme will reduce the evaporation duty by 50% and will result in a build-up of lignin and cellulose in the liquid product by about 2 times.

Examples 8-11 Pretreatment and Hydrogenolysis Experiments Pre-Treatment

A reactor (a 200 ml stirred autoclave) was charged with 10 g of poplar wood (oven dried at 105° C., sieve fraction 1-2 mm) and 90 g of solvent. The solvent used in Example 8 was a water and ethanol mixture. In Examples 9 to 11 mixtures of a water and acetic acid were used. Oxygen was removed by nitrogen flushing. The pre-treatment of the poplar wood with the solvent was carried out for 1-5 h at 180-200° C. Afterwards, the solid residue was washed with a mixture of 50/50 w/w water/ethanol until no colour change of the liquid was observed. Subsequently, the solid residue was dried by flushing nitrogen at room temperature until no weight change of the solid residue was observed. The composition of the resulting biomass samples, to be used as feedstock for the hydrogenolysis experiments, is presented.

Hydrogenolysis

Catalytic hydrogenolysis experiments were carried out in a 45 ml batch autoclave. A preheated fluidized sand bed and a water bath allowed for rapid heating and rapid cooling, respectively. The autoclave was equipped with a hollow shaft stirrer, a pressure transducer and a thermocouple located on the bottom of vessel.

The reactor was charged with 14.25 g of deionised water, 0.75 g of biomass, 0.021 g of retro-aldol catalyst (sodium polytungstate), 0.086 g of hydrogenation catalyst (Raney-Ni, dry basis) and 0.3 g of acetic acid plus NaOH to buffer the solution to pH 3.3. Prior to use, Raney-Ni was thoroughly washed with deionized water until the pH of the washing water became neutral. The reactor was sealed and flushed twice with nitrogen, twice with hydrogen and pressurized to about 60 bar. The stirrer was then started (1300 rpm) and the autoclave submerged in the fluidized sand bed. The reaction time was started once the reactor attained a temperature of 245° C.

The residence time was limited to 1 h, as no further glycol yield increase was observed at longer residence times.

After completion the autoclave was rapidly cooled applying a water bath and depressurized, opened and the reactor content obtained. A liquid sample was taken and subjected to high performance liquid chromatography (HPLC) analysis and pH measurement (Metrohm LL Unitrode Pt 1000 pH). Remaining catalyst and unconverted residue were collected in a separate bottle by flushing the reactor with deionized water.

TABLE 3

| Example | 8 | 9 | 10 | 11 |
|---|---|---|---|---|
| Pretreatment conditions | | | | |
| Feedstock | Poplar | Poplar | Poplar | Poplar |
| Temperature (° C.) | 200 | 180 | 180 | 180 |
| Reaction time (min) | 180 | 300 | 60 | 60 |
| Solvent | Ethanol | Acetic acid | Acetic Acid | Acetic Acid |
| Solvent fraction (wt. %) | 50 | 50 | 70 | 89.3 |
| Water fraction (wt. %) | 50 | 50 | 30 | 10.7 |

TABLE 3-continued

| Example | 8 | 9 | 10 | 11 |
|---|---|---|---|---|
| Mixture biomass & solvent | | | | |
| Biomass loading (wt. %) | 9.3 | 9.6 | 9.6 | 9.6 |
| Composition - pre-treated, washed and dried | | | | |
| Cellulose (wt. %) | 77.6 | 79.2 | 83.1 | 77.5 |
| Hemi-cellulose (wt. %) | 5.9 | 6.5 | 3.2 | 6.7 |
| Total (poly)-saccharides (wt. %) | 83.5 | 85.8 | 86.4 | 84.2 |
| Total lignin (wt. %) | 6.2 | 11.5 | 3.6 | 1.5 |

TABLE 4

| Example | 8 | 9 | 10 | 11 |
|---|---|---|---|---|
| Hydrogenolysis conditions | | | | |
| Temperature (° C.) | 245 | 245 | 245 | 245 |
| Residence time (min) | 60 | 60 | 60 | 60 |
| Solid loading (wt %) | 5 | 5 | 5 | 5 |
| Feedstock Particle Size (mm) | 0.05 | 0.05 | 0.05 | 0.05 |
| Raney Nickel (g) | 0.086 | 0.086 | 0.086 | 0.086 |
| SPT (Na6W12O39) (g) | 0.021 | 0.021 | 0.021 | 0.021 |
| Initial H2 Pressure (bar) | 61.0 | 60.8 | 60.0 | 59.9 |
| Final reactor pressure (bar) | 47.3 | 50.3 | 51.3 | 51.9 |
| Final pH | 3.3 | 3.2 | 3.3 | 3.4 |
| Product Yields (poly)-alcohols | | | | |
| Ethylene-glycol (wt. %) | 25.1 | 28.3 | 32.3 | 21.2 |
| Propylene-glycol (wt. %) | 7.3 | 6.6 | 6.8 | 9.1 |
| 1.2-Butanediol (wt %) | 3.9 | 7.5 | 6.1 | 6.2 |
| 1.2-Hexanediol (wt. %) | 0.34 | 0.86 | 0.26 | 0.47 |
| Glycerol (wt %) | 1.9 | 1.4 | 2.5 | 2.4 |
| m-Erythritol (wt %) | 1.8 | 2.4 | 4.5 | 2.9 |
| Xylitol (wt. %) | 1.5 | 0.6 | 1.3 | 1.4 |
| Sorbitol + Mannitol (wt. %) | 4.8 | 8.6 | 17.9 | 15.9 |
| Light alcohols | | | | |
| Methanol | 0.90 | 2.5 | 1.7 | 2.7 |
| Ethanol | 5.3 | 4.4 | 4.0 | 5.0 |
| 1-Propanol | 0.76 | 0.71 | 0.47 | 0.92 |
| 2-Propanol | 0.86 | 1.71 | 0.14 | 0.23 |
| 1-Butanol | 0.09 | 0.06 | 0.06 | |
| 2-Butanol | 0.5 | 0.8 | 0.3 | 0.6 |
| Light-Alcohols, total (% w) | 8.5 | 10.2 | 6.6 | 9.5 |

The hydrogenolysis was performed using biomass that was pre-treated with water/alcohol or with water/acid, followed by washing and drying.

Light alcohols were formed during hydrogenolysis. The light alcohols may be recycled to step (a).

Example 12

Figure 2:
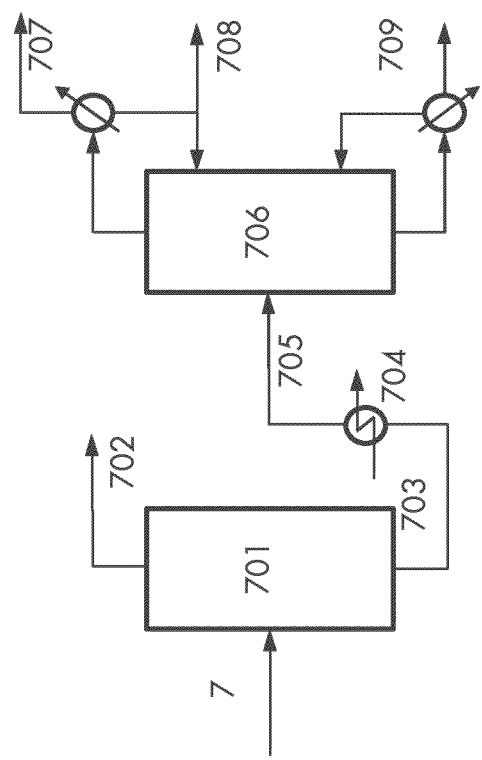
FIG. 2 shows a block flow process scheme used in Example 12.

FIG. 2 shows a block scheme that may be used after the block scheme of FIG. 1. Reactor effluent 7, obtained by hydrogenolysis of glucose (see FIG. 1), is depressurized in a gas/liquid separator 701, to separate a vapor phase stream 702 from a liquid stream 703. The liquid stream 703 is cooled in heat exchanger 704 providing a feed stream 705 which is fed into a distillation column 706. A stream of non-condensing components 707 and condensing components mainly comprising light alcohols 708 is obtained from the upper part of the column. The bottom stream 709 can be further processed to obtain purified components.

The total organics fraction in this particular example is 42.7% w in stream 7. The combined fraction of methanol, ethanol, 1-propanol, 2-propanol, 1-butanol and 2-butanol is 2.7% w, which represents 6.4% w of the total organics fraction.

Aspen(+) modeling results of stream compositions are presented in Table 5. Stream 708 is mainly composed of light alcohols, with 15% water present. The majority of the light alcohols are recovered in stream 702 (after condensation, not described in further detail) and in stream 708 (Table 5).

This example shows that a mixture of light alcohols can be recovered and recycled. This does not require large amounts of energy or complex equipment.

The recovered mixture of light alcohols is useful for recycle in a process as claimed (see also FIG. 1). Lignin will dissolve in it.

TABLE 5

Aspen(+) modeling results, stream compositions (mass fractions).

| Stream description | 7 | 702 | 703 | 705 | 707 | 708 | 709 |
|---|---|---|---|---|---|---|---|
| Phase | Mixed | Vapor | Liquid | Liquid | Vapor | Liquid | Liquid |
| Temperature (deg. C.) | 203 | 186 | 186 | 165 | 40 | 40 | 195 |
| Pressure (bara) | 100 | 12 | 12 | 12 | 12 | 12 | 12 |
| Mass Flows (t/year) | 1000 | 45.9 | 954.1 | 954.1 | 0.031 | 13.1 | 940.9 |
| Mass Fractions | | | | | | | |
| methanol | 0.0038 | 0.0135 | 0.0033 | 0.0033 | 0.0126 | 0.0688 | 0.0024 |
| ethanol | 0.0125 | 0.0630 | 0.0101 | 0.0101 | 0.0511 | 0.4755 | 0.0036 |
| 1-propanol | 0.0102 | 0.0549 | 0.0081 | 0.0081 | 0.0148 | 0.2996 | 0.0040 |
| 2-propanol | 4.46E−05 | 0.000334038 | 3.06E−05 | 3.06E−05 | 0.000196061 | 0.0021491 | 1.10E−06 |
| 1-butanol | 0.0006 | 0.0033 | 0.0005 | 4.66E−04 | 1.15E−05 | 0.0005 | 0.0005 |
| 2-butanol | 3.48E−05 | 0.0003 | 2.39E−05 | 2.39E−05 | 7.63E−05 | 0.0016 | 1.73E−06 |
| H2O | 0.5549 | 0.7708 | 0.5445 | 0.5445 | 0.0091 | 0.1500 | 0.5500 |
| H2 | 4.97E−04 | 1.07E−02 | 8.02E−06 | 8.02E−06 | 0.2143 | 7.78E−05 | 0 |
| methane | 1.36E−03 | 0.0289 | 3.67E−05 | 3.67E−05 | 0.6368 | 0.0012 | 0 |
| ethane | 1.66E−04 | 0.0035 | 4.63E−06 | 4.63E−06 | 0.0375 | 0.0002 | 0 |
| propane | 2.30E−04 | 0.0049 | 5.97E−06 | 5.97E−06 | 0.0234 | 0.0004 | 0 |
| MEG | 0.2802 | 0.0324 | 0.2921 | 0.2921 | 0 | 0 | 0.2962 |
| MPG | 0.0281 | 6.47E−03 | 0.0292 | 2.92E−02 | 0 | 0 | 0.0296 |
| 1,2-butanediol | 0.0047 | 1.24E−03 | 0.0049 | 4.92E−03 | 0 | 0 | 0.0050 |
| 1,2-pentanediol | 0.0003 | 7.34E−05 | 0.0003 | 2.73E−04 | 0 | 0 | 0.0003 |

TABLE 5-continued

Aspen(+) modeling results, stream compositions (mass fractions).

| Stream description | 7 | 702 | 703 | 705 | 707 | 708 | 709 |
|---|---|---|---|---|---|---|---|
| 1,2-hexanediol | 0.0135 | 0.0039 | 0.0139 | 0.0139 | 0 | 0 | 0.0141 |
| glycerol | 0.0057 | 2.80E−05 | 0.0060 | 5.99E−03 | 0 | 0 | 0.0061 |
| erythritol | 0.0283 | 7.68E−06 | 0.0297 | 0.0297 | 0 | 0 | 0.0301 |
| sorbitol | 0.0340 | 2.08E−08 | 0.0356 | 3.56E−02 | 0 | 0 | 0.0361 |
| isosorbide | 0.0024 | 7.55E−05 | 0.0025 | 2.54E−03 | 0 | 0 | 0.0026 |
| acetic acid | 0.0004 | 2.77E−04 | 0.0004 | 4.38E−04 | 0 | 0 | 0.0004 |
| lactic acid | 0.0002 | 8.98E−06 | 0.0003 | 0.0003 | 0 | 0 | 0.0003 |

TABLE 6

Component recovered from feed (% recovered).

| Description Recovered from feed (% w) | 702 | 703 | 705 | 707 | 708 | 709 | 702 + 708 |
|---|---|---|---|---|---|---|---|
| methanol | 16.4 | 83.6 | 83.6 | 0.0 | 23.8 | 59.8 | 40.2 |
| ethanol | 23.1 | 76.9 | 76.9 | 0.0 | 49.9 | 27.0 | 73.0 |
| 1-propanol | 24.7 | 75.3 | 75.3 | 0.0 | 38.4 | 36.9 | 63.1 |
| 2-propanol | 34.4 | 65.6 | 65.6 | 0.0 | 63.2 | 2.3 | 97.7 |
| 1-butanol | 25.5 | 74.5 | 74.5 | 0.0 | 1.1 | 73.4 | 26.6 |
| 2-butanol | 34.5 | 65.5 | 65.5 | 0.0 | 60.8 | 4.7 | 95.3 |
| H2O | 6.4 | 93.6 | 93.6 | 0.0 | 0.4 | 93.3 | 6.7 |
| H2 | 98.5 | 1.5 | 1.5 | 1.3 | 0.2 | 0.0 | 98.7 |
| methane | 97.4 | 2.6 | 2.6 | 1.4 | 1.1 | 0.0 | 98.6 |
| ethane | 97.3 | 2.7 | 2.7 | 0.7 | 2.0 | 0.0 | 99.3 |
| propane | 97.5 | 2.5 | 2.5 | 0.3 | 2.2 | 0.0 | 99.7 |
| MEG | 0.5 | 99.5 | 99.5 | 0.0 | 0.0 | 99.5 | 0.5 |
| MPG | 1.1 | 98.9 | 98.9 | 0.0 | 0.0 | 98.9 | 1.1 |
| 1,2-butanediol | 1.2 | 98.8 | 98.8 | 0.0 | 0.0 | 98.8 | 1.2 |
| 1,2-pentanediol | 1.3 | 98.7 | 98.7 | 0.0 | 0.0 | 98.7 | 1.3 |
| 1,2-hexanediol | 1.3 | 98.7 | 98.7 | 0.0 | 0.0 | 98.7 | 1.3 |
| glycerol | 0.0 | 100.0 | 100.0 | 0.0 | 0.0 | 100.0 | 0.0 |
| erythritol | 0.0 | 100.0 | 100.0 | 0.0 | 0.0 | 100.0 | 0.0 |
| sorbitol | 0.0 | 100.0 | 100.0 | 0.0 | 0.0 | 100.0 | 0.0 |
| isosorbide | 0.1 | 99.9 | 99.9 | 0.0 | 0.0 | 99.9 | 0.1 |
| acetic acid | 2.9 | 97.1 | 97.1 | 0.0 | 0.0 | 97.1 | 2.9 |
| lactic acid | 0.2 | 99.8 | 99.8 | 0.0 | 0.0 | 99.8 | 0.2 |

As shown in the Examples section above, the presently disclosed method for pre-treating lignocellulosic-containing feedstock has numerous advantages over the prior art. Therefore, the disclosed subject matter provides an improved method suitable for the pre-treatment of lignocellulosic-containing feedstock for the use in production of glycols.

The foregoing description, for purpose of explanation, has been described with reference to specific embodiments. However, the illustrative discussions above are not intended to be exhaustive or to limit embodiments of the disclosed subject matter to the precise forms disclosed. Many modifications and variations are possible in view of the above teachings. The embodiments were chosen and described in order to explain the principles of embodiments of the disclosed subject matter and their practical applications, to thereby enable others skilled in the art to utilize those embodiments as well as various embodiments with various modifications as may be suited to the particular use contemplated.

We claim:

1. A process for the preparation of glycols from a lignocellulosic solid biomass comprising cellulose, hemicellulose and lignin in a reactor system, said process comprising:
a) contacting the lignocellulosic solid biomass with an organic solvent comprising a low boiling point alcohol, and a pre-treatment acid, at a temperature ranging from about 80 to about 220° C. and a pressure ranging from 1 to 50 bar (absolute) for a time ranging from about 5 minutes to about 2 hours to obtain a first mixture;
b) separating the first mixture obtained in step (a) into a pre-treated solid residue comprising cellulose and a liquid stream comprising dissolved lignin and hemicellulose;
c) subjecting the pre-treated solid residue to a hydrogenolysis reaction and generating a glycols stream, a lights stream and a heavies stream, wherein the lights stream comprises a co-product organic solvent and an in-situ produced pre-treatment acid;
d) recycling at least a part of the lights stream to step (a), wherein the co-product organic solvent in the lights stream comprises a first portion of the organic solvent;
e) separating at least part of the liquid stream from step b) to produce a second portion of the organic solvent and a solid residue that comprises lignin and hemicellulose; and
f) recycling at least a part of the second portion of the organic solvent to step (a);
wherein the first mixture has greater than about 20 wt % water; and
wherein the pre-treatment acid comprises at least one selected from the group consisting of formic acid, acetic acid, propionic acid, butyric acid, glycolic acid, lactic acid, and combinations thereof which is/are at least partially generated in-situ in step (a).

2. The process of claim 1, wherein the pre-treated solid residue comprises pre-treatment acid and the process further comprises removing pre-treatment acid from the pre-treated solid residue by washing, drying or combinations thereof to produce an acid-removed pre-treated solid residue and recycling the removed pre-treatment acid to step (a).

3. The process of claim 1, wherein the pre-treated solid residue comprises lignin and the process further comprises removing the lignin from the pre-treated solid residue by washing to produce a lignin-removed pre-treated solid residue and a liquid stream comprising lignin, and recycling the liquid stream comprising lignin to step (a).

4. The process according to claim 1, wherein the pre-treatment acid further comprises at least one selected from the group consisting of hydrochloric acid, sulfuric acid, boric acid, nitric acid, phosphoric acid, hydroxysulfonic acid, citric acid, benzoic acid, α-hydroxysulfonic acids, and mixtures thereof.

5. The process according to claim 1, wherein the pH of the lignocellulosic solid biomass, the organic solvent, and the pre-treatment acid solution in step (a) is maintained in the range from 2-6.

6. The process according to claim 1, wherein subjecting the pre-treated solid residue to a hydrogenolysis reaction comprises contacting the pre-treated solid residue, a soluble retro-Aldol catalyst, and an optional hydrogenolysis acid in a reactor under hydrogenation conditions.

7. The process of claim 6, wherein the pre-treatment acid and the hydrogenolysis acid are the same.

8. The process according to claim 1, wherein the separating the liquid stream (b) comprises evaporation by heating the liquid stream at a temperature in the range of from 50 to 150° C.

9. The process according to claim 1, wherein the low boiling point alcohol is at least one of methanol, ethanol, iso-propanol and n-propanol.

10. The process according to claim 1, further comprising recycling at least a part of the heavies stream to step (c).

11. The process according to claim 1, further comprising separating and/or washing the lignin/hemicellulose solid to produce an aqueous hemicellulose stream and a lignin solid.

12. The process of claim 11, further comprising converting the aqueous hemicellulose stream to furfural.

13. The process according to claim 1, wherein a part of the liquid stream from step (b) is recycled to step (a).

14. The process according to claim 2, wherein drying comprises heating, reducing pressure, or combinations thereof.

* * * * *